United States Patent
Lykke et al.

(10) Patent No.: US 7,141,016 B2
(45) Date of Patent: Nov. 28, 2006

(54) SYSTEMS AND METHODS FOR MONITORING GASTROINTESTINAL SYSTEM

(75) Inventors: Michael Lykke, Hellerup (DK); Michael Madsen, Kgs. Lyngby (DK); Martin T. Gerber, Maple Grove, MN (US); Warren L. Starkebaum, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 319 days.

(21) Appl. No.: 10/423,594

(22) Filed: Apr. 25, 2003

(65) Prior Publication Data

US 2004/0215068 A1    Oct. 28, 2004

(51) Int. Cl.
*A61B 5/00* (2006.01)
(52) U.S. Cl. ............... 600/300; 600/361; 600/365; 600/593
(58) Field of Classification Search ........... 600/593, 600/300, 361, 365
See application file for complete search history.

(56) References Cited

U.S. PATENT DOCUMENTS

| | | | |
|---|---|---|---|
| 4,844,076 A | | 7/1989 | Lesho et al. |
| 5,279,607 A | | 1/1994 | Schentag et al. |
| 5,395,366 A | | 3/1995 | D'Andrea et al. |
| 6,132,372 A | * | 10/2000 | Essen-Moller ............ 600/431 |
| 6,240,312 B1 | | 5/2001 | Alfano et al. |
| 6,338,345 B1 | | 1/2002 | Johnson et al. |
| 6,491,643 B1 | | 12/2002 | Katzman et al. |
| 2002/0099310 A1 | * | 7/2002 | Kimchy et al. ............ 600/587 |
| 2002/0132226 A1 | | 9/2002 | Nair et al. |
| 2002/0173718 A1 | * | 11/2002 | Frisch et al. ............ 600/424 |
| 2002/0198470 A1 | | 12/2002 | Imran et al. |
| 2003/0020810 A1 | | 1/2003 | Takizawa et al. |
| 2003/0191430 A1 | * | 10/2003 | D'Andrea et al. ......... 604/66 |

FOREIGN PATENT DOCUMENTS

| | | |
|---|---|---|
| EP | 1 260 176 A2 | 11/2002 |
| GB | 2 373 330 | 9/2002 |

OTHER PUBLICATIONS

Wong et al., "Gastric Emptying of Water in Term Pregnancy" Anesthesiology 2002; 96: 1935-1400.*
Cucchiara et al. "Gastric Emptying Delay and Gastric Electrical Derangement in IDDM" Diabetics Care, vol. 21, No. 3, Mar. 1998.*
Tanenberg et al. "Continuous Glucose Monitoring Syste: A new approach to the diagnosis of diabetic gastroparesis" Diabetes Technology & Therapeutics, vol. 2, Suppl. 1, 2000.*
Cucchiara et al. "Gastric Emptying Delay and Gastric Electrical Derangement in IDDM" Diabetes Care, vol. 21, No. 3, Mar. 1998, pp. 438-443.*

(Continued)

*Primary Examiner*—Charles A Marmor, II
*Assistant Examiner*—Patricia Mallari
(74) *Attorney, Agent, or Firm*—Mary P. Bauman; Medtronic, Inc.

(57) ABSTRACT

In general, the invention is directed to systems and methods for monitoring the gastrointestinal system of a patient. In one embodiment, the invention includes techniques for monitoring the emptying of the patient's stomach. The techniques may employ glucose monitoring, pH monitoring with a consumable sensor, of monitoring the position of a consumable sensor as it exits the stomach. Consumable sensors may be employed to sense conditions, such as temperature or bile concentration, in other segments of the gastrointestinal system. The invention also includes systems for tracking the position of one or more consumable sensors as the sensors transit the gastrointestinal system, and monitoring the conditions sensed by the sensors.

29 Claims, 5 Drawing Sheets

OTHER PUBLICATIONS

Jones et al. "Predictors of Delayed Gastric Emptying in Diabetes" Diabetes Care, vol. 24, No. 7, Jul. 2001, pp. 1264-1269. obtained at http://care.diabetesjournals.org/cgi/reprint 24/7/1264.*

Horowitz et al. "Gastric Emptying in Diabetes: clinical significance and treatment" Diabetic Medicine, 19, pp. 177-194 (2002). obtained at http://www.blackwell-synergy.com/doi/pdf/10.1046/j. 1464-5491.2002.00658.x.*

Tanenberg et al., "Continuous Glucose Monitoring System: A New Approach to the Diagnosis of Diabetic Gastroparesis" (Diabetes Technol Ther. 2000;2Suppl 1:S73-80).

Gonlachanvit et al., "Effect of Altering Gastric Emptying on Postprandial Plasma Glucose Concentrations Following a Physiologic Meal in Type-II Diabetic Patients" (Digestive Diseases and Sciences, vol. 48, No. 3, (Mar., 2003), pp. 488-497).

Mojaverian et al. "Estimation of Gastric Residence Time of the Heidelberg Capsule in Humans: Effect of Varying Food Composition" (Gastroenterology, vol. 89, No. 2, (1985), pp. 392-397).

Alioth et al., "Application of Dual Radiotelemetric Technique in Studying Drug-Drug Interaction Between Diclofenac Sodium and Ranitidine HCl in Volunteers" (Dec., 1992) (3 pgs.).

Cucchiara et al., "Gastric Emptying Delay and Gastric Electrical Derangement in IDDM" (Diabetes Care, vol. 21, No. 3, (Mar., 1998), pp. 438-443).

Groning et al., "Estimation of the Gastric Residence Time of Magnetic Dosage Forms Using the Heidelberg Capsule" (Institute for Pharmaceutical Technology, University of Munster, Germany, vol. 51, No. 5, (May, 1996), 3 pgs.

Wong et al., "Gastric Emptying of Water in Term Pregnancy" (Anesthestology, vol. 96, No. 6, (Jun., 2002), pp. 1395-1400.

Steinbach, JH., "Fluoroscopic Observations of Transit of Solid Particles in the Gut," Nerogastroenterology and Motility, vol. 14, Issue 4, p. 450 (2002).

* cited by examiner

SYSTEMS AND METHODS FOR MONITORING GASTROINTESTINAL SYSTEM

FIELD OF THE INVENTION

The invention relates to medical devices and methods, and in particular, to medical devices and methods that monitor the gastrointestinal system.

BACKGROUND

Many techniques exist for observing or monitoring the gastrointestinal (GI) system of a patient. For example, a patient may be asked to perform a barium swallow while the progress of the barium is observed radiographically. A gastric emptying scan involves consumption of a radioactive meal, and observation by x-ray. Scintigraphy, another widely used technique, involves use of a gamma camera and a radiolabeled test meal. The patient may be given a drug to consume, and the patient's blood may be monitored for concentration of the drug. The patient's GI activity may be monitored by an ultrasound procedure, or by monitoring the patient's electrical impedance, or by monitoring isotopes in the breath of the patient.

Each of these techniques has significant drawbacks. Many of them require large equipment and are limited to a hospital setting. Many of them also use radiation or drugs as part of the monitoring, and many cannot be safely repeated without a risk of harm to the patient.

Table 1 lists patents that disclose systems or devices that monitor the GI system or a portion thereof. One of the patents, for example, describes a breath test analyzer that determines a gastric emptying rate in response to the presence of isotope labeled products in the patient's breath following ingestion of an isotope labeled substance. Some of the patents describe methods or devices for monitoring pH levels in certain locations, of for sending capsules to make measurements at or deliver medication to particular sites within the GI system.

| Patent Number | Inventors | Title |
| --- | --- | --- |
| 6,491,643 | Katzman, et al. | Breath test analyzer |
| 6,338,345 | Johnson, et al. | Submucosal prosthesis delivery device |
| 6,240,312 | Alfano, et al. | Remote-controllable, micro-scale device for use in in vivo medical diagnosis and/or treatment |
| 5,395,366 | D'Andrea, et al. | Sampling capsule and process |
| 5,279,607 | Schentag, et al. | Telemetry capsule and process |
| 4,844,076 | Lesho, et al. | Ingestible size continuously transmitting temperature monitoring pill |

The patents listed in Table 1 above are hereby incorporated by reference herein in their entirety. As those of ordinary skill in the art will appreciate readily upon reading the Summary of the Invention, Detailed Description of the Preferred Embodiments and Claims set forth below, some of the devices and methods disclosed in the patent of Table 1 may be modified advantageously by using the techniques of the present invention.

SUMMARY OF THE INVENTION

The invention has certain objects. That is, various embodiments of the present invention provide solutions to one or more problems existing in the prior art with respect to monitoring the gastrointestinal (GI) system of a patient. Such problems include, but are not limited to, the drawbacks of monitoring techniques in the prior art. Many monitoring techniques are unpleasant or inconvenient to the patient, or require a hospital visit. Many techniques are also not repeatable because they employ radiation or drugs that may be harmful in large doses.

Various embodiments of the present invention have the object of solving at least one of the foregoing problems. For example, one object of the invention is to effectively monitor one or more aspects of the GI system of a patient. Gastric emptying is one aspect of the GI system that may be monitored by applying the techniques of the invention. With information obtained by monitoring gastric emptying, a patient's physician may diagnose decreased, delayed, or rapid gastric emptying without the use of radiolabeled meal.

A further object of the invention, however, is to monitor processes other than or in addition to gastric emptying. Some embodiments of the invention reflecting a condition of the GI system, such as pH level, temperature, bile concentration, and the like. Other embodiments of the invention track the progress and position of one or more consumable, i.e., ingestible, sensors through the GI system.

One of the objects of the invention is that the invention helps a physician understand the GI system of the patient. The invention provides the physician with data that allow the physician to diagnose conditions associated with gastric emptying or other problems with the GI system.

Various embodiments of the invention may possess one or more features capable of fulfilling the above objects. In general, the invention provides methods for monitoring gastric emptying that may be employed separately or in concert. By monitoring blood glucose, or by monitoring pH levels with a consumable sensor, or by tracking the process of one or more consumable sensors through the GI system, the invention facilitates understanding of the patient's gastric emptying. In addition, the invention provides methods and systems fir observing other regions of the GI system and the conditions therein. The invention provides a system, for example, for computing the position of one or more consumable sensors as the sensors transit the GI system.

In comparison to known implementations of monitoring the GI system, various embodiments of the present invention may provide one or more advantages. For example, the invention does not necessarily require a hospital visit or specialized hospital equipment. On the contrary, some of the procedures of the invention may be performed during an office visit. Nor does the invention require administration by specially trained personnel, such as a radiologist.

The invention provides considerable freedom and enjoyment of life for the patient. In some of the embodiments to be described below, the equipment may be easily carried with patient as he goes about his business. In addition, the techniques and systems described below should be well tolerated by most patients, and do not involve high levels of harmful radiation or drugs that cause adverse effects. Consequently, the techniques of the invention may be repeated with little risk of harm to the patient.

The details of one or more embodiments of the invention are set forth in the accompanying drawings and the description below. Other features, objects, and advantages of the invention will be apparent from the description and drawings, and from the claims.

DETAILED DESCRIPTION OF THE PREFERRED EMBODIMENTS

Figure 1:
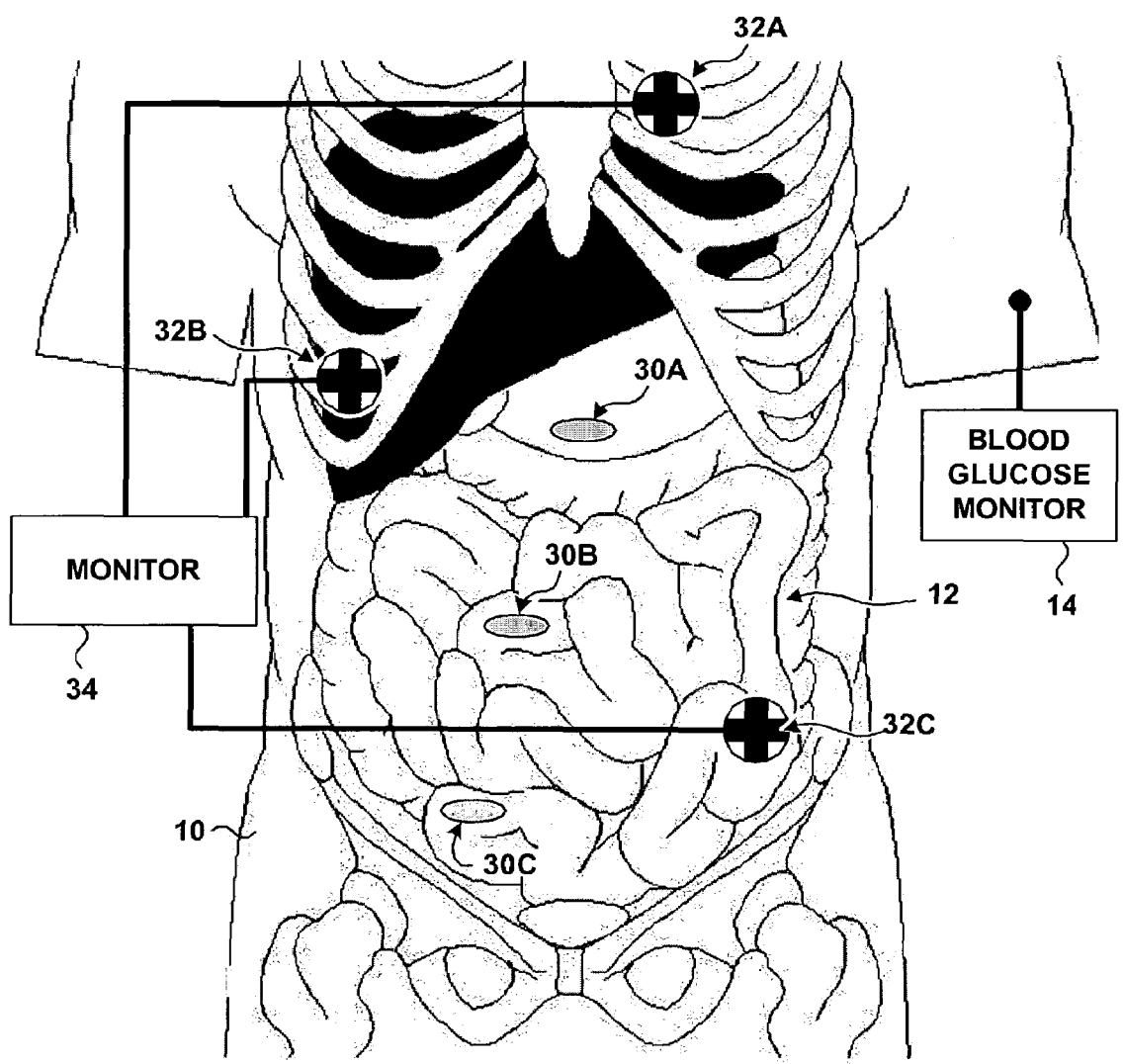
FIG. 1 is a schematic view of a human torso illustrating the gastrointestinal tract and devices for monitoring the gastrointestinal tract.

FIG. 1 is a schematic view of the torso of a patient 10, in which the gastrointestinal (GI) tract 12 is visible. FIG. 1 illustrates devices and systems for monitoring the GI tract.

One device for monitoring GI tract 12 is a blood glucose monitor 14. Blood glucose monitor 14 measures blood glucose levels continuously or at frequent intervals, such as every five minutes. Blood glucose monitor 14 records the measurements and the time that each measurement was made. An example of such a monitor is the commercially available Meteoric MiniMed Continuous Glucose Monitoring System.

Blood glucose monitor 14 monitors GI tract 12 by monitoring the blood glucose concentration in patient 10 following consumption of a meal by patient 10. The meal may be consumed at a known time and may include a known amount of glucose. The glucose in the meal does not break down in the stomach of patient 10. The glucose begins to be broken down when the meal enters the duodenum, however, and blood glucose monitor 14 detects the resulting change in blood chemistry when glucose is broken down. In particular, blood glucose monitor 14 detects a change in blood glucose concentration that occurs when the meal leaves the stomach of patient 10.

Because blood glucose monitor 14 records the time that blood glucose concentration changes, it is possible to estimate the time that gastric emptying occurs in patient 10. Because the time of consumption of the meal is known, blood glucose monitor 14 or the physician may estimate the elapsed time between consumption of the meal and gastric emptying. This elapsed time may serve as the basis for a diagnosis such as gastro paresis, which is often present in diabetics, or rapid gastric emptying.

Figure 2:
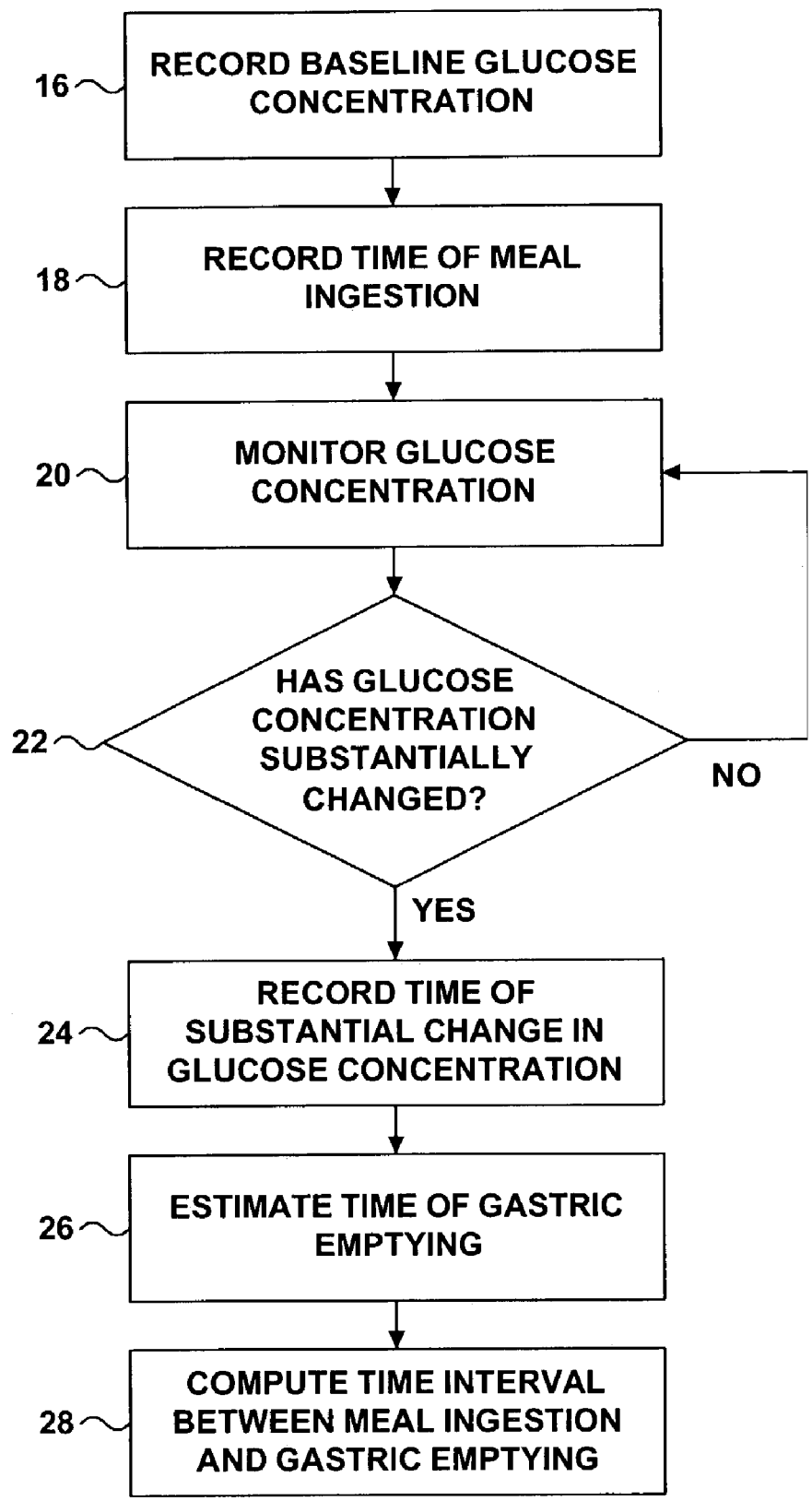
FIG. 2 is a flow diagram illustrating a technique for estimating the time of gastric emptying as a function of monitored glucose concentration.

FIG. 2 is a flow diagram illustrating a technique for estimating the time of gastric emptying as a function of monitored glucose concentration. Although the techniques shown in FIG. 2 may be applied by a processor in a computer (not shown in the figures) that downloads data from blood glucose monitor 14, the techniques may also be applied by a processor in blood glucose monitor 14. For simplicity, the techniques will be described as applied by blood glucose monitor 14.

Blood glucose monitor 14 optionally records a baseline glucose concentration in patient 10 (16). The baseline may be recorded prior to consumption of the meal, while the meal is being consumed, or shortly after consumption of the meal. When patient 10 consumes the meal, blood glucose monitor 14 records the time of ingestion (18) and begins monitoring glucose concentration (20).

When glucose concentration substantially changes (22), blood glucose monitor 14 records the time of substantial change in glucose concentration (24). Blood glucose monitor 14 may determine that there has been a substantial change with respect to the baseline concentration, or may determine that there has been a substantial change by application of other criteria. For example, blood glucose monitor 14 may determine that there has been a substantial change based upon the detected blood glucose concentration and upon the known glucose concentration of the meal.

Blood glucose monitor 14 estimates the time of gastric emptying (26) as a function of the monitored glucose concentration. In general, the substantial change in glucose concentration indicates that gastric emptying has occurred. Blood glucose monitor 14 may further compute the time interval between meal ingestion and gastric emptying (28).

Returning to FIG. 1, another set of devices for monitoring GI system 12 includes one or more consumable devices 30A, 30B, 30C (hereinafter 30). Consumable device 30 is configured to be ingested by patient 10 and to transit GI system 12. Consumable device 30 may be constructed from an inert or non-digestible material, or may include a protective non-digestible coating, that causes no adverse effects during an ordinary transit through GI system 12.

In addition, consumable device 30 is configured to transmit one or more signals from inside GI system 12. A typical consumable device 30 includes a transmitter that actively transmits a wireless radio frequency (RF) signal that may be detected by one or more receivers 32A, 32B, 32C (hereinafter 32). The signal may define an amplitude and a phase, and the signal may encode any information using any analog or digital coding technique.

Receivers 32 may be deployed external to patient 10, e.g., on the skin of patient 10. Each receiver 32 may include a mounting element to mount the receiver on the body of patient 10. Mounting elements may comprise an adhesive patch, for example, or a garment worn by patient 10. The positions of receivers 32 shown in FIG. 1 are for purposes of illustration, and receivers 32 may be deployed at other sites around the body of patient 10. Although three receivers 32 are depicted in FIG. 1, more or fewer receivers 32 may be deployed.

Receivers 32 supply data to a monitor 34. The supplied data may include signals detected by or generated by receivers 32. Monitor 34 includes a processor that records the data, records the time that the data are received from receivers 32, and processes the data. The data may include position data, i.e., data reflecting the position of one or more receivers 32 in GI system 12, or physiological data reflecting the physical characteristics of GI system 12. Monitor 34 may be small and portable, and may be carried with patient 10. Monitor 34 may, for example be mounted on a belt worn by patient 10.

In one embodiment, consumable device 30 includes a sensor. For purposes of illustration, the sensor will be assumed to be a pH sensor that responds to the acidity of the environment. A consumable pH sensor 30 generates a signal as a function of the pH level of the environment. A receiver 32 receives the signal and supplies the signal to monitor 34. By monitoring the signal, monitor 34 can estimate the time that gastric emptying occurs in patient 10. Gastric emptying is indicated by a substantial increase in pH.

An example of a consumable pH sensor 30 is the commercially available Meteoric Bravo pH Monitoring System. Sensor 30, which may be about the size of a gelcap, generates a signal as a function of acid levels and transmits the signals to a receiver 32 via RF wireless communication. In a typical application, receiver 32 may be included in monitor 34, which may be worn by patient 10.

Figure 3:
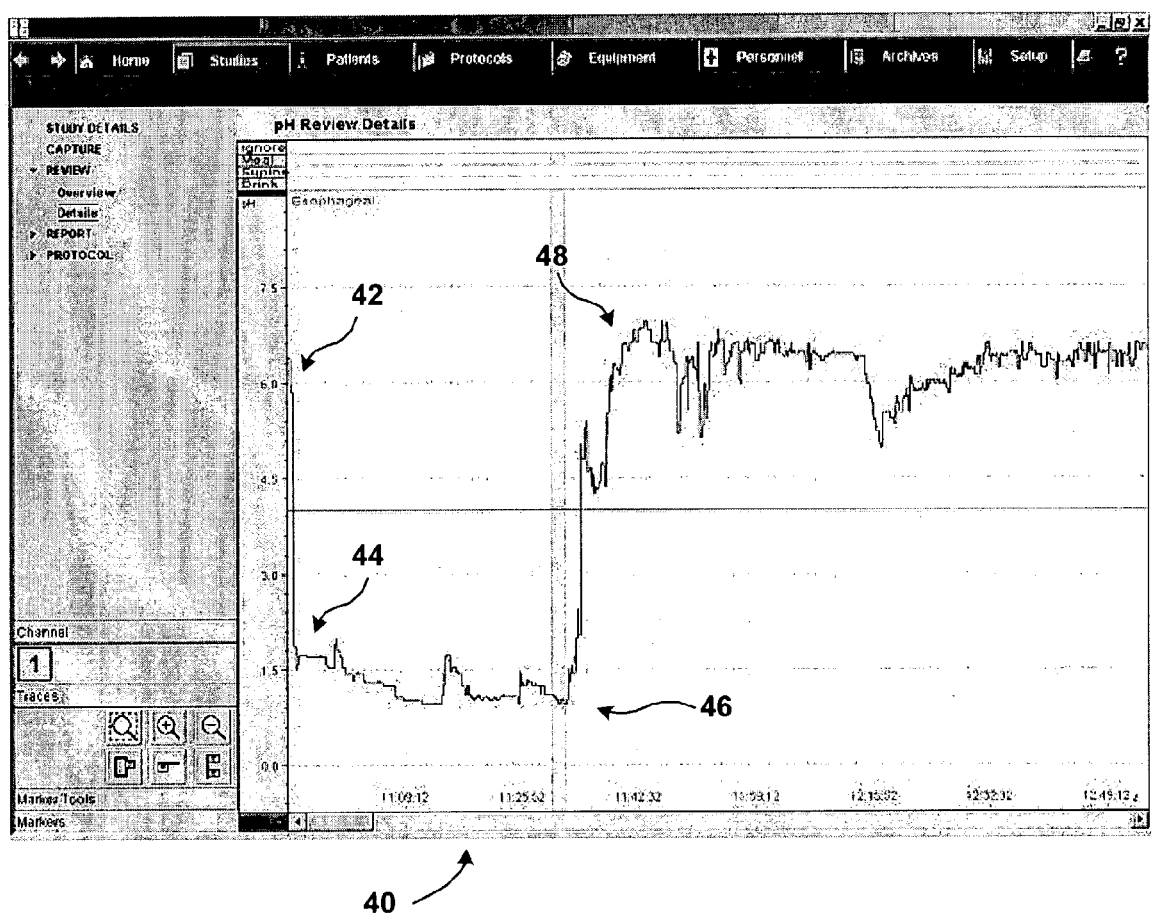
FIG. 3 is an illustrative screen shot showing a graphical representation of pH level data from a consumable pH sensor.

FIG. 3 is a screen shot 40 of data captured from a consumable pH sensor 30. At initial consumption (42), consumable pH sensor 30 transmits a signal that reflects a substantially neutral pH level. When consumable pH sensor 30 reaches the stomach, however, the pH level falls dramatically from neutral and becomes highly acidic due to the stomach's secretion of hydrochloric acid. As a result, the signals reflect a pH level in a range of 1 to 2 pH (44). The signals continue to reflect a pH level in a range of 1 to 2 pH as long as consumable pH sensor 30 remains in the stomach.

When consumable pH sensor 30 exits the stomach, sodium bicarbonate secreted into the lumen of the duodenum neutralizes the acidic contents emptied from the stomach. The pH level around consumable pH sensor 30 therefore rises (46), and eventually settles into a range of approximately 6 to 7 pH (48). The substantial increase in pH occurs after consumable pH sensor 30 has left the stomach. Accordingly, the time that gastric emptying occurs in patient 10 may be estimated, based upon monitoring a substantial increase in a pH signal from consumable pH sensor 30 in GI system 12 of patient 10.

Figure 4:
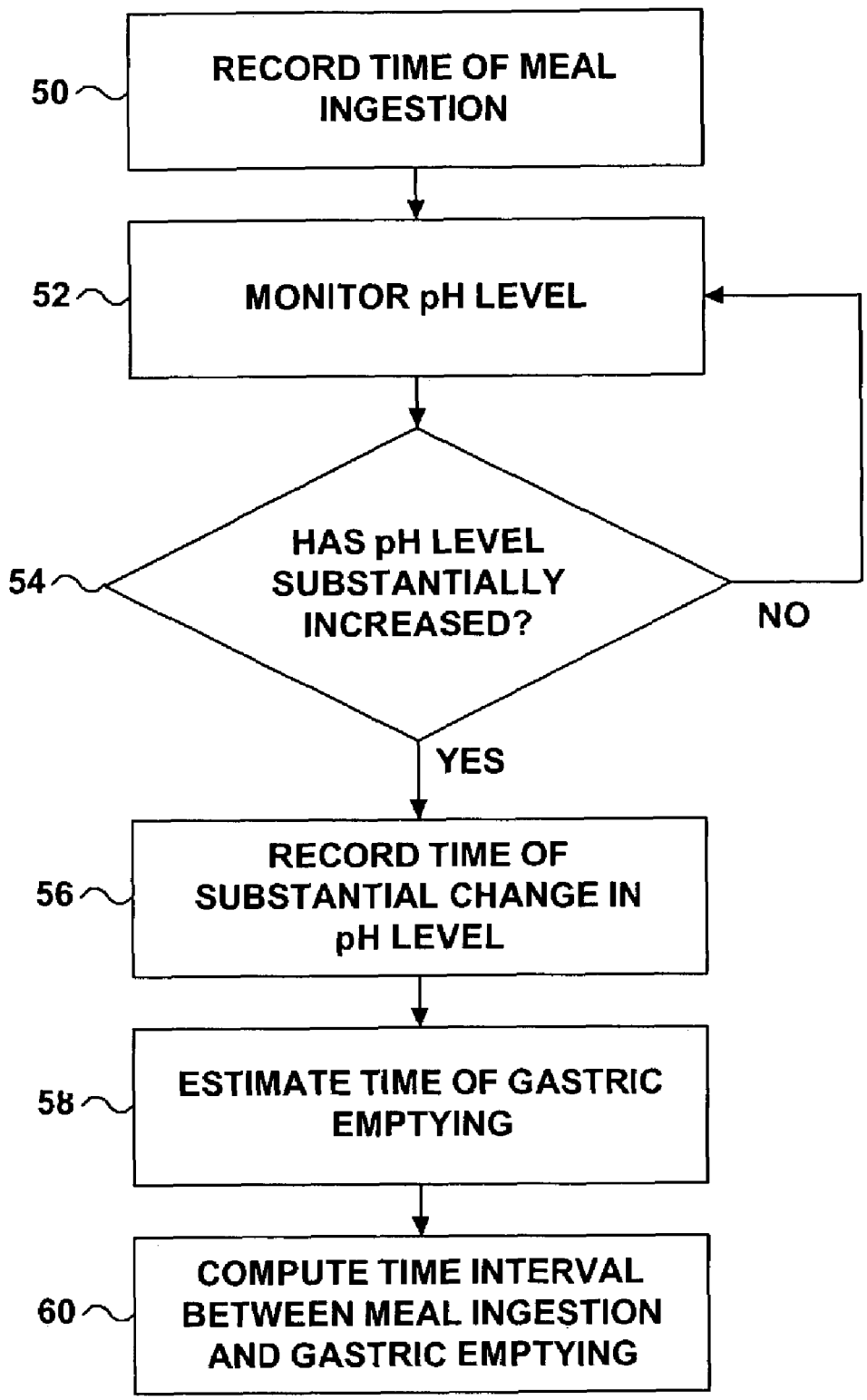
FIG. 4 is a flow diagram illustrating a technique for estimating the time of gastric emptying as a function of monitored pH level.

FIG. 4 is a flow diagram illustrating a technique for estimating the time of gastric emptying as a function of monitored pH level. Although the techniques shown in FIG. 4 may be applied by a processor in a computer (not shown in the figures) that downloads data from monitor 34, the techniques may also be applied by a processor in monitor 34. For simplicity, the techniques will be described as applied by monitor 34.

Monitor 34 optionally records the time of ingestion of a consumable pH sensor 30, ingested as a part of a meal (50). Monitor 34 begins monitoring pH levels (52). As shown in FIG. 3, pH levels stay in a range of approximately 1 to 2 pH when consumable pH sensor 30 is in the stomach.

When the pH level substantially rises (54), monitor 34 records the time of substantial change in pH level (56) and estimates the time of gastric emptying (58) as a function of the pH level. The pH level may eventually rise to a range of approximately 6 to 7 pH, but monitor 34 may determine that gastric emptying has occurred when there has been a substantial increase in pH level. Monitor 34 may further compute the time interval between meal ingestion and gastric emptying (60).

Consumable sensor 30 may generate a sensor signal, i.e., a signal in response to sensed conditions other than acidity level. For example, consumable sensor 30 may generate a sensor signal as a function of temperature, pressure, moisture or impedance. Consumable sensor 30 may generate a sensor signal as a function of concentration of a particular substance in GI system 12, such as bile. By monitoring the signals, monitor 34 may monitor any of several conditions in GI system 12.

In variations of this technique, patient 10 may consume more than one consumable pH sensor 30, and monitor 34 may monitor the conditions surrounding each consumable pH sensor 30. Consumable pH sensors 30 may indicate changes in conditions at different times, which may reflect physiological conditions of interest. For example, several pH sensors ingested at approximately the same time may leave the stomach at different times. The data from the sensors may support an estimate a time interval over which gastric emptying occurs, as well as a gastric emptying rate.

When multiple consumable sensors 30 are ingested, sensors 30 need not be responsive to the same conditions. Patient 10 may ingest pH sensors and bile sensors, for example. Furthermore, the sizes of consumable sensors 30 need not be uniform, and each may be sized differently. It has been observed that different size boluses or capsules transit a GI system at different rates. Use of differently sized sensors 30 may therefore provide useful information about rates of transit of bulk through GI system 12.

When multiple consumable sensors 30 are ingested, each sensor is configured to transmit an identification signal in addition to a signal reflecting a condition. Monitor 34 uses the identification signal to distinguish one consumable sensor 30 from another.

At the direction of his physician, patient 10 may consume several consumable sensors over time. Patient 10 may, for example, consume a set of sensors with breakfast, a second set of sensors at lunch, and a third set of sensors at supper. Monitor 34 may monitor each sensor as it transits GI system 12, until the sensor leaves the body of patient 10 by defecation.

In another embodiment of the invention, multiple consumable sensors 30 transmit position signals. For example, each signal may define an amplitude and a phase used for locating the position of each consumable sensor 30. The position of each consumable sensor 30 may be determined by triangulation with receivers 32, e.g., by processing position signal phase delays. Receivers 32 may be deployed at various sites on the body of patient 10 to facilitate location of consumable sensors 30 based upon position signals. Monitor 34, which may be carried with patient 10, records the position of each consumable sensor 30 over time.

Figure 5:
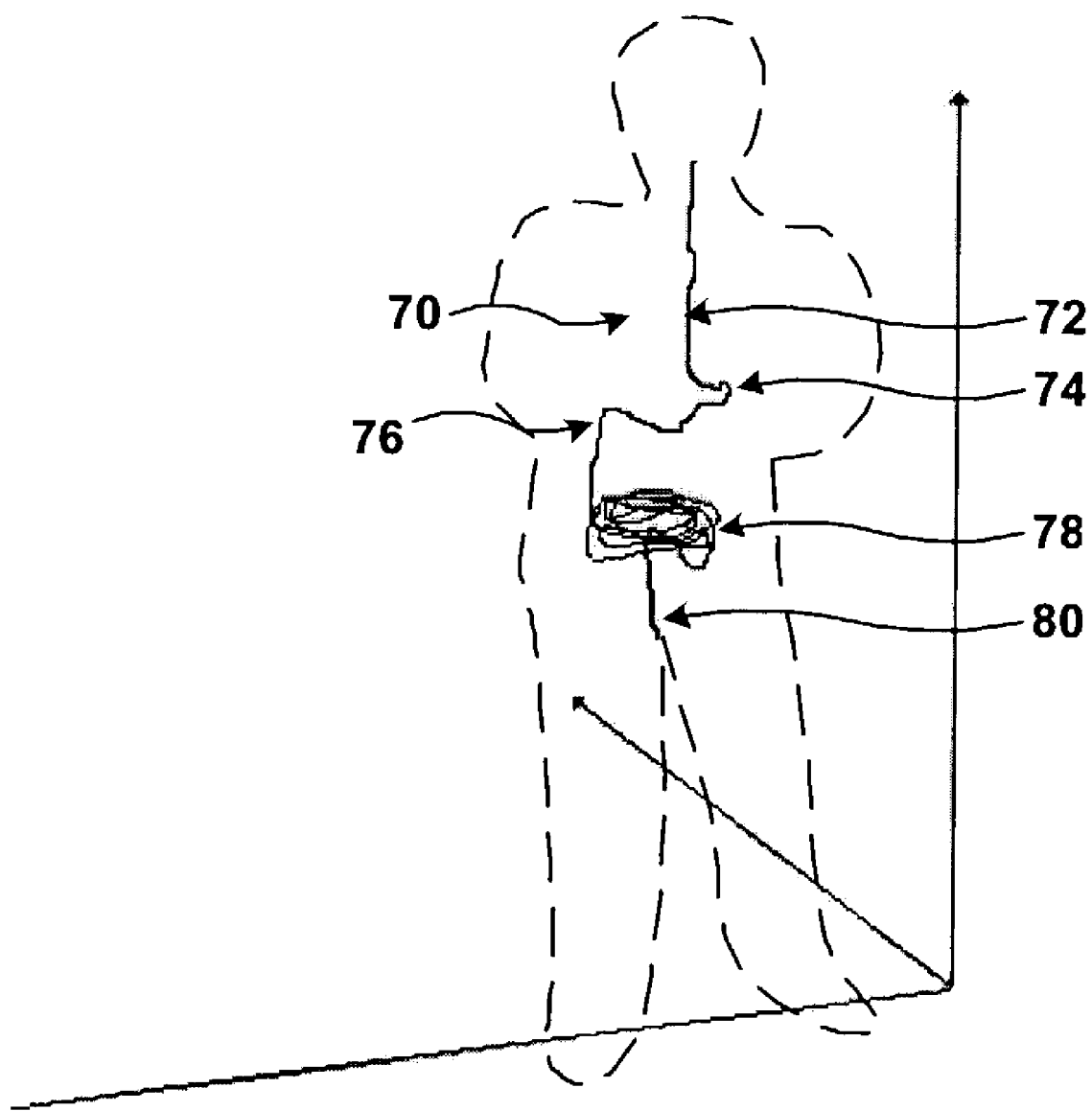
FIG. 5 is a graphical representation of position data based upon position signals from a consumable sensor that transited the gastrointestinal system of a patient.

FIG. 5 is a graphical representation of position data 70 from the position signals of a consumable sensor 30 monitored over a period of several hours. The path traced out by position data 70 indicates the location of consumable sensor 30. For example, the path may be used to identify the times when consumable sensor 30 was in the esophagus (72), fundus of stomach (74), duodenum (76), small bowel (78) or rectum (80).

In addition to position signals, each sensor 30 may transmit one or more signals reflecting a condition, such as pH level, temperature, bile concentration, and the like. Moreover, the use of consumable sensors 30 may be combined with blood glucose monitor 14, to obtain a very detailed overview of the gastric emptying process in patient 10.

The systems and techniques described above help a physician understand the GI system of the patient. With the data provided by the invention, the physician can diagnose conditions associated with gastric emptying or other problems with the GI system.

The techniques and systems described above do not necessarily require a hospital visit or specialized hospital equipment, and need not be administered by specially trained personnel. Some of the procedures may be performed during an office visit. Other techniques, such as the monitoring of the position on one or more consumable sensors, may be performed at any time. In some of the described embodiments, the sensors, receivers and monitors are ambulatory, meaning that the patient may carry the sensors, receivers and monitors with him as he goes about his business. The sensors are ordinarily discarded during defecation, and need not be returned. The data collected by the monitor may be downloaded or otherwise reviewed by the physician at the convenience of the physician and the patient.

Furthermore, the techniques and systems described above are well tolerated by the patient. Certain procedures, such as a barium swallow, are inconvenient and unpleasant. Many patients find the barium solution disagreeable in spite of flavoring that may be added. The consumable sensors, by contrast, may be ingested with a pleasant meal, and may be sized to be about as large as typical medicines or vitamin pills.

The techniques described above do not use high levels of harmful radiation or drugs that cause adverse effects. Consequently, the techniques may be repeated with little risk of harm to the patient.

The preceding specific embodiments are illustrative of the practice of the invention. It is to be understood, therefore, that other expedients known to those skilled in the art or disclosed herein may be employed without departing from the invention or the scope of the claims. For example, the present invention further includes within its scope methods of making and using systems for tracking the position of one or more consumable devices as described herein. Moreover, the consumable devices need not include independently powered transmitters, but may include transmitters that resonate in response to signals generated by one or more receivers. The consumable devices may also generate signals transmitted by a medium other than radio, such as ultrasound. These and other embodiments are within the scope of the following claims.

This invention claimed is:

1. A method comprising:
   monitoring a blood glucose concentration in a patient following consumption of a meal by the patient; and
   estimating the time that gastric emptying occurs in the patient as a function of the blood glucose concentration.

2. The method of claim 1, further comprising recording the time of consumption of the meal.

3. The method of claim 1, wherein estimating the time that gastric emptying occurs comprises:
   recording a baseline blood glucose concentration;
   recording the time that the monitored blood glucose concentration substantially changes from the baseline concentration; and
   estimating the time that gastric emptying occurs as the time when the blood glucose concentration substantially changes from the baseline concentration.

4. The method of claim 1, further comprising:
   monitoring a position of a device in the gastrointestinal system, the device consumed by the patient with the meal; and
   estimating the time that gastric emptying occurs as a function of the position.

5. The method of claim 1, further comprising:
   monitoring a pH signal from a device in a gastrointestinal system, the device consumed by the patient with the meal; and
   estimating the time that gastric emptying occurs as a function of the pH signal.

6. The method of claim 1, wherein the meal includes a known amount of glucose.

7. A method comprising:
   monitoring a first pH signal from a first device in a gastrointestinal system of a patient;
   monitoring a second pH signal from a second device in the gastrointestinal system of the patient; and
   estimating the time that gastric emptying occurs in the patient as a function of the first and second pH signals.

8. The method of claim 7, wherein estimating the time that gastric emptying occurs comprises estimating the time that at least one of the first or second pH signals indicates a substantial pH increase from a range of approximately 1 to 2 pH.

9. The method of claim 8, wherein estimating the time that gastric emptying occurs comprises estimating the time that at least one of the first or second pH signals indicates a pH increase from a range of approximately 1 to 2 pH to a range of approximately 6 to 7 pH.

10. The method of claim 7, further comprising:
    monitoring a blood glucose concentration in the patient following consumption of a meal by the patient; and
    estimating the time that gastric emptying occurs as a function of the blood glucose concentration.

11. The method of claim 7, further comprising:
    monitoring a position of at least one of the first and second devices device in the gastrointestinal system; and
    estimating the time that gastric emptying occurs as a function of the position.

12. A system comprising:
    a first consumable device including a transmitter, the first consumable device configured to transit the gastrointestinal system of a patient and to transmit a first signal;
    a second consumable device configured to transit the gastrointestinal system and to transmit a second signal;
    at least two receivers to receive the first and second signals signal from the first and second consumable devices when the first and second consumable devices transit the gastrointestinal system; and
    a processor to compute positions of the first and second consumable devices in the gastrointestinal system as a function of the received first and second signals.

13. The system of claim 12, wherein the first consumable device is sized differently from the second consumable device.

14. The system of claim 12, wherein the signals define an amplitude and a phase, and wherein the processor computes the positions of the consumable devices as a function of the amplitudes and the phases of the received signals.

15. The system of claim 12, wherein at least one of the first and second consumable devices comprises a sensor to generate a sensor signal in response to a condition.

16. The system of claim 15, wherein the sensor is at least one of a pH sensor, a temperature sensor, a pressure sensor, a moisture sensor, an impedance sensor, and a bile concentration sensor.

17. The system of claim 12, wherein the first consumable device is configured to transmit a first identification signal and the second consumable device is configured to transmit a second identification signal.

18. A method comprising:
    monitoring a first position signal from a first device in a gastrointestinal system of a patient;
    monitoring a second position signal from a second device in the gastrointestinal system;
    estimating the time that gastric emptying occurs in the patient as a function of first and second position signals.

19. The method of claim 18, further comprising monitoring a condition signal from the first device.

20. The method of claim 19, wherein the condition signal varies as function of at least one of pH level, temperature, pressure, moisture, impedance and bile concentration.

21. The method of claim 18, further comprising monitoring a blood glucose concentration in the patient following consumption of a meal by the patient.

22. The method of claim 18, wherein monitoring the first position signal comprises monitoring the first position signal with at least two receivers configured to receive the first position signal.

23. The method of claim 22, wherein monitoring the first position signal comprises computing the position of the first device as a function of the first position signal received by the receivers.

24. A system comprising:
- a first consumable device including a transmitter, the first consumable device configured to transit the gastrointestinal system of a patient and to transmit a first pH signal;
- a second consumable device configured to transit the gastrointestinal system of the patient and to transmit a second pH signal;
- at least one receiver to receive the first and second pH signals signal from the first and second consumable devices when the first and second consumable devices transit the gastrointestinal system; and
- a processor to estimate the time that gastric emptying occurs in the patient as a function of the first and second pH signals.

25. The system of claim 24, wherein the first consumable device is configured to transmit a first identification signal and the second consumable device is configured to transmit a second identification signal.

26. The system of claim 24, wherein the first consumable device is sized differently from the second consumable device.

27. The system of claim 26, wherein the sensor signal comprises at least one of a temperature signal, a pressure signal, a moisture signal, an impedance.

28. The system of 24, wherein the first consumable device comprises a sensor to generate a sensor signal in response to a condition. signal, and a bile concentration signal.

29. The system of claim 24, wherein the first consumable device is further configured to transmit a position signal, and wherein the processor is further configured to compute a position of the first consumable device in the gastrointestinal system as a function of the position signal.

* * * * *

UNITED STATES PATENT AND TRADEMARK OFFICE
CERTIFICATE OF CORRECTION

PATENT NO. : 7,141,016 B2  Page 1 of 1
APPLICATION NO. : 10/423594
DATED : November 28, 2006
INVENTOR(S) : Michael Lykke It is certified that error appears in the above-identified patent and that said Letters Patent is hereby corrected as shown below:

Column 8, line 19, delete "device".

Column 8, line 30, delete "signals".

Column 10, line 13, immediately following "an impedance" add -- signal, and a bile concentration signal --.

Column 10, line 16, delete "an impedance signal, and a bile contraction signal".

Signed and Sealed this

Tenth Day of April, 2007

JON W. DUDAS
*Director of the United States Patent and Trademark Office*